United States Patent [19]

Cimarusti et al.

[11] 3,971,776
[45] July 27, 1976

[54] THIO-β-LACTAM PENICILLINS

[75] Inventors: Christopher M. Cimarusti, Hamilton, N.J.; Paul Wojtkowski, Wilmington, Del.; Joseph E. Dolfini, Cincinnati, Ohio

[73] Assignee: E. R. Squibb & Sons, Inc., Princeton, N.J.

[22] Filed: Feb. 19, 1975

[21] Appl. No.: 551,221

[52] U.S. Cl. .............................. 260/239.1; 424/271
[51] Int. Cl.² ............. C07D 499/44; C07D 499/46; C07D 499/48
[58] Field of Search .................... 260/239.1

[56] References Cited
UNITED STATES PATENTS
3,632,578   1/1972   Chauvette .................... 260/239.1

OTHER PUBLICATIONS
Henry–Logan et al., J. Heterocyclic Chem. vol. 5 pp. 433–434 (1968).

*Primary Examiner*—Gerald A. Schwartz
*Attorney, Agent, or Firm*—Lawrence S. Levinson; Merle J. Smith

[57] ABSTRACT

Thio-β-lactam penicillins of the general formula

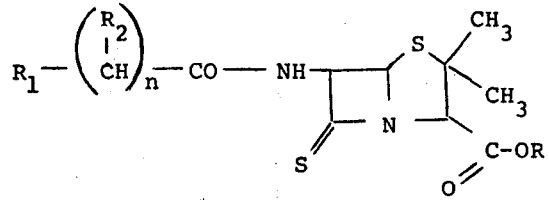

wherein R is hydrogen, lower alkyl, phenyl-lower alkyl, trihaloethyl, alkali metal or alkaline earth metal; $R_1$ is hydrogen, lower alkyl, cycloalkyl, phenyl, lower alkoxyphenyl, phenoxy, phenyl-lower alkyl or certain heterocyclic groups; $R_2$ is hydrogen, amino, carboxy or ureido; and $n$ is 0 or 1; are useful as antimicrobial agents.

8 Claims, No Drawings

THIO-β-LACTAM PENICILLINS

SUMMARY OF THE INVENTION

This invention relates to new thio-β-lactam penicillins of the formula

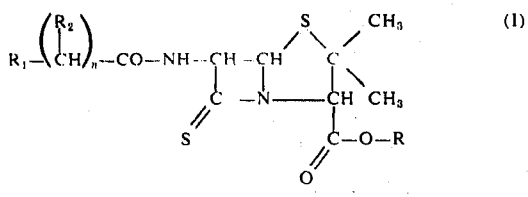

R represents hydrogen, lower alkyl, phenyl-lower alkyl, trihaloethyl, alkali metal or alkaline earth metal; $R_1$ represents hydrogen, lower alkyl, saturated and unsaturated cycloalkyl, phenyl, lower alkoxyphenyl, phenoxy, phenyl-lower alkyl or certain heterocyclic groups; $R_2$ represents hydrogen, amino, carboxy or ureido, and $n$ is 0 to 1.

The preferred members within each group are as follows: R is hydrogen, alkali metal or trichloroethyl especially hydrogen, sodium or potassium; $R_1$ is hydrogen, phenyl, thienyl or furyl, especially phenyl or thienyl; $R_2$ is hydrogen, amino or carboxy, especially hydrogen or amino, and $n$ is 1.

DETAILED DESCRIPTION OF THE INVENTION

The various groups represented by the symbols have the meanings defined below and these definitions are retained throughout this specification.

The lower alkyl groups are straight or branched chain hydrocarbon radicals from methyl to heptyl, for example, methyl, ethyl, propyl, isopropyl, butyl, isobutyl, t-butyl, amyl or the like. The one to four carbon groups are preferred, especially methyl and ethyl. The lower alkoxy groups include such alkyl groups linked through an oxygen, methoxy being preferred.

The cycloalkyl groups include saturated and unsaturated cyclic alkyl groups having three to seven carbon atoms and one or two double bonds, for example, cyclopropyl, cyclobutyl, cyclopentyl, cyclohexyl, cycloheptyl, cyclobutenyl, cyclopentenyl, cyclohexenyl, cyclohexadienyl and the like. The five and six carbon members are preferred and among the unsaturated members; the 1,4-cyclohexadien-1-yl and 1-cyclohexen-1-yl groups are preferred.

The phenyl-lower alkyl groups include a phenyl group attached to a lower alkyl group as described above. Benzyl and phenethyl are preferred.

The four common halogens are included in the term "halo," chlorine and bromine, especially chlorine being preferred.

The heterocyclics (having 5 or 6 atoms exclusive of hydrogen which are carbon, sulfur, nitrogen and oxygen, no more than two being other than carbon), namely thienyl, furyl, oxazolyl, isoxazolyl and thiazolyl, as well as these heterocyclics with the substituents phenyl, halophenyl (particularly dichlorophenyl), halo or lower alkyl (particularly methyl and ethyl) are included. The substituted heterocyclics include particularly halophenyl (lower alkyl) especially 3-(2,6-dichlorophenyl)-5-methylisoxazole and 3-(o-chlorophenyl-5-methylisoxazole.

In addition to hydrogen, R can be a salt forming ion, e.g., metal ions, like the alkali metal ions such as sodium or potassium or the alkaline earth metal ions such as calcium or magnesium.

The new penicillins of this invention can be produced by several alternate routes. A preferred method comprises converting a known penicillin, i.e., one having oxygen instead of sulfur in the 7-position corresponding to formula

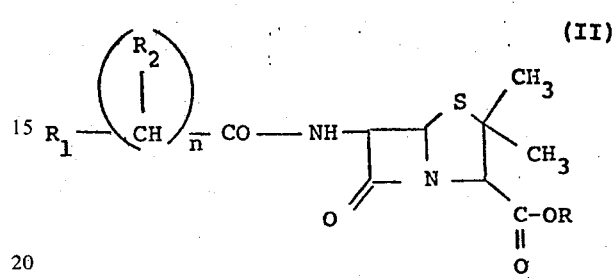

by reaction with boron sulfide. This reaction is effected by treating the penicillin of formula II with an excess of boron sulfide, e.g., about two moles of the boron sulfide to about one mole of penicillin compound, in an inert organic solvent such as chloroform, dichloromethane, benzene or the like. An elevated temperature, e.g., in the range of about 30° to about 80° C. is used. It is desirable, during this reaction, to protect the carboxy group with a protective group which is then easily removed. Preferred is the formation of the 2,2,2-trichloroethyl ester [which is effected by the method of Chauvette et al., J. Org. Chem. 36, 1959 (1971)]. The protecting group is removed after the sulfur atom is introduced by treatment with a metal-acid pair, e.g., an excess of zinc metal in aqueous acetic acid. Other protecting groups which can be used include, for example, dichloroethyl or methyl ester. The product is then isolated and purified by conventional procedures, e.g., filtration, evaporation of solvent, chromatography, etc.

An alternate method comprises first treating a readily available and readily cleavable penicillin, such as benzylpenicillin or phenoxymethylpenicillin or the like, with boron sulfide as described above. Then the product, optionally with the protecting group still in place, is cleaved by known methods, e.g., by intermediate formation of an imino chloride followed by hydrolysis to remove the acyl group in the 6-position. This provides a new intermediate, which is also part of this invention, having the formula

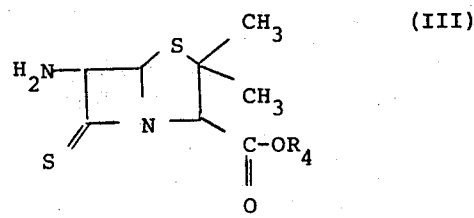

wherein $R_4$ is trihaloethyl, dichloroethyl, methyl or hydrogen. This intermediate can then be acylated with the appropriate acid halide or acid anhydride by conventional techniques to obtain the product of formula I having the desired acyl group in the 6-position.

According to this embodiment the reaction between the 6-amino-7-thiopenicillanic acid of formula III and the acid is effected, for example, by dissolving or suspending the latter in an inert organic solvent such as chloroform, methylene chloride, dioxane, benzene or the like, and adding, at about room temperature or below, about an equimolar amount of an anhydride forming reagent, e.g., ethyl chloroformate, benzoyl-chloride or the like, or other activating compound such as dicyclohexyl-carbodiimide, along with a salt forming organic base such as triethylamine, pyridine or the like, followed, after an interval, by the addition of 6-aminopenicillanic acid or derivative. The product of the reaction is then isolated by conventional procedures, e.g., by concentration or evaporation of the solvent.

Further process details are also provided in the illustrative examples.

Certain of the compounds of this invention may exist in different optically active forms. The various stereoisomeric forms as well as the racemic mixtures are within the scope of the invention.

The compounds of this invention are useful as antimicrobial agents because of their activity against organisms such as *Streptococcus pyogenes* and *Candida albicans*. They can be used to combat infections due to organisms such as those named above, and in general may be utilized in a manner similar to penicillin G and other penicillins. For example, a compound of formula I or a physiologically acceptable salt thereof can be used in various animal species in an amount of about 1 to 200 mg/kg, daily, orally or parenterally, in single or two to four divided doses to treat infections of bacterial origin, e.g., 5.0 mg/kg is effective in mice. Up to about 600 mg. of a compound of formula I or a physiologically acceptable salt thereof is incorporated in an oral dosage form such as tablets, capsules or elixirs or in an injectable form in a sterile aqueous vehicle prepared according to conventional pharmaceutical practice.

The following examples are illustrative of the invention and are preferred embodiments. They also serve as models for additional variations which are produced in the same manner by appropriate substitution of the starting material. All temperatures are in degrees celsius.

EXAMPLE 1

3,3-Dimethyl-6β-[(phenoxyacetyl)amino]-7-thioxo-4-thia-1-azabicyclo[3.2.0]heptane-2-carboxylic acid 2,2,2-trichloroethyl ester 2,2,2-Trichloroethyl 6-(phenoxyacetamido)penicillanate is prepared according to the method of Chauvette, et al., J. Org. Chem., 36, 1259 (1971). This ester (4 g. 8.33 mmoles) is dissolved in 50 ml. of dry chloroform and boron sulfide (2 g., 17 mmoles) are added. The mixture is allowed to reflux overnight under nitrogen. The mixture is filtered and the solvent is removed under reduced pressure. The residue is placed on 80 g. of silica gel and eluted with chloroform to remove polar reaction products. The material eluted from the column is purified by preparative silica gel thin layer chromatography using methylene chloride to give 60 mg. of yellow gum. Elution of this through 1.5 g. of silica gel with benzene gives 44 mg. (1%) of 3,3-dimethyl-6β-[(phenoxyacetyl)amino]-7-thioxo-4-thia-1-azabicyclo[3.2.0]heptane-2-carboxylic acid, 2,2,2-trichloroethyl ester as a yellow foam.

EXAMPLE 2

3,3-Dimethyl-6β-[(phenoxyacetyl)amino]-7-thioxo-4-thia-1-azabicyclo[3.2.0]heptane-2-carboxylic acid The ester from Example 1 (16 mg. 0.03 mmoles) is dissolved in 1 ml. of 90% aqueous acetic acid and zinc dust (20 mg. 30 mmoles) is added. The mixture is allowed to stir at 0° for 2 hours. The reaction mixture is poured into 5ml. of water and 20 ml. of ethyl acetate. The layers are separated and the organic layer is washed with 5 ml. of cold water. Cold water (10 ml.) is added and the pH is adjusted to 8 with cold aqueous sodium hydroxide. The aqueous layer is separated and treated with 20 ml. of cold ethyl acetate. The pH is adjusted to 2 by the addition of concentrated hydrochloric acid. The organic layer is separated, dried over magnesium sulfate, filtered, and the solvent is removed under reduced pressure to yield 4 mg. (25%) of 3,3-dimethyl-6β-[(phenoxyacetyl)amino]-7-thioxo-4-thia-1-azabicyclo[3.2.0]-heptane-2-carboxylic acid as a yellow gum.

EXAMPLE 3

3,3-Dimethyl-6-amino-7-thioxo-4-thia-1-azabicyclo[3.2.0]-heptane-2-carboxylic acid, 2,2,2-trichloroethyl ester The product of Example 1 (50 mg., 0.144 mmol) is dissolved in dry benzene (10 ml.), then dry pyridine (16 mg., 0.212 mmoles) and phosphorus pentachloride (44 g., 0.212 mmoles) are added. The resultant solution is heated to 65° nitrogen for two hours. The benzene is then removed in vacuo and replaced with methanol (6 ml.). This mixture is stored at room temperature under nitrogen overnight. The methanol is removed under reduced pressure and replaced by a mixture of water-tetrahydrofuran. This is stirred at room temperature for 15 minutes and the aqueous solution is treated with ethyl acetate and the pH is adjusted to 7 with sodium hydroxide. The ethyl acetate layer is separated, washed with water and dried over magnesium sulfate. Evaporation of the solvent under vacuum yields 3,3-dimethyl- 6-amino-7-thioxo-4-thia-1-azabicyclo[3.2.0]heptane-2-carboxylic acid, 2,2,2-trichloroethyl ester.

EXAMPLE 4

3,3-Dimethyl-6β-[(phenylacetyl)amino]-7-thioxo-4-thia-1-azabicyclo[3.2.0]heptane-2-carboxylic acid a)
3,3-Dimethyl-6β-[(phenylacetyl)amino]-7-thioxo-4-thia-1-azabicyclo[3.2.0]heptane-2-carboxylic acid, 2,2,2-trichloroethyl ester.

A solution of the product of Example 3 in 5 ml. of dichloromethane is cooled to 0° and 0.2 mmole of triethylamine and 0.2 mmole of phenylacetyl chloride are added. After 2 hours, the solution is washed with water, dilute hydrochloric acid, water, dilute sodium bicarbonate solution, dried, and evaporated to give 3,3-dimethyl-6β-[(phenylacetyl)-amino]-7-thioxo-4-thia-1-azabicyclo[3.2.0]heptane-2-carboxylic acid, 2,2,2-trichloroethyl ester.

b. 3,3-Dimethyl-6β-[(phenylacetyl)amino]-7-thioxo-4-thia-1-azabicyclo[3.2.0]heptane-2-carboxylic acid Treatment of the trichloroethyl ester prepared in part a with zinc in aqueous acetic acid according to the procedure of Example 2 gives 3,3-dimethyl-6β-[(phenylacetyl)amino]-7-thioxo-4-thia-1-azabicyclo[3.2.0]heptane-2-carboxylic acid.

The potassium salt is formed by reacting the above product with potassium ethylhexanoate.

The following additional products are made by the procedure of Example 1.

TABLE

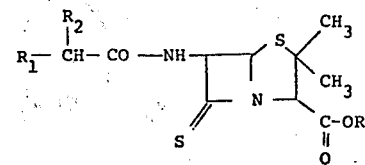

| Example | R | $R_1$ | $R_2$ |
|---|---|---|---|
| 5 | $CH_3-$ | H | H |
| 6 | $C_2H_5-$ | $CH_3-$ | H |
| 7 | $CH_2CCl_3$ | $C_3H_7-$ | H |
| 8 | $-CH_2CCl_3$ | $C_6H_5CH_2-$ | H |
| 9 | $-CH_2CCl_3$ | $C_6H_5CH_2-$ | H |
| 10 | $-CH_2CCl_3$ | $C_6H_5-$ | H |

Following the procedure of Example 4, and substituting the acylating agent listed in the last column for phenylacetyl chloride, the following are obtained:

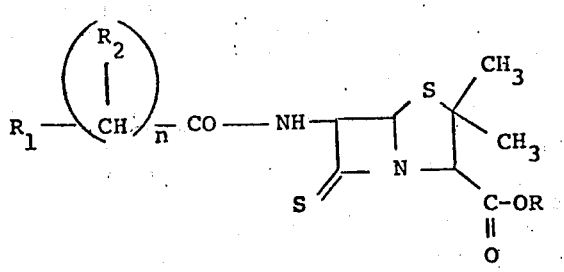

| Example | R | $R_1$ | n | $R_2$ | Acylating Agent |
|---|---|---|---|---|---|
| 11 | Na | $C_6H_5-$ | 1 | $-NHCONH_2$ | φ-CH(NH-C(=O)-NH_2)-COOH |
| 12 | K | (thienyl) | 1 | $-NH_2$ | (thienyl)-CH(NH_3^+)-C(=O)Cl, Cl^- |
| 13 | H | $CH_3$-(thienyl) | 1 | $-NH_2$ | $CH_3$-(thienyl)-CH(NH_3^+)-C(=O)Cl, Cl^- |
| 14 | H | (isoxazolyl) | 1 | H | (isoxazolyl)-CH_2-C(=O)Cl |
| 15 | H | (thienyl) | 1 | H | (thienyl)-CH_2-C(=O)Cl |
| 16 | H | (furyl) | 1 | H | ((furyl)-CH_2-C(=O))_2O |

-continued
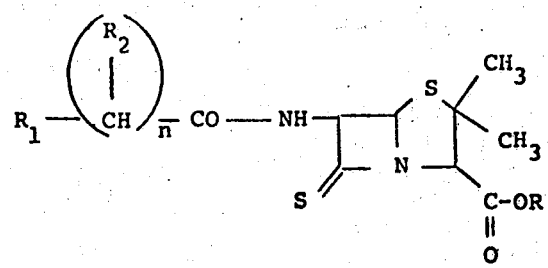
| Example | R | $R_1$ | n | $R_3$ | Acylating Agent |
|---|---|---|---|---|---|
| 17 | H | oxazole | 1 | H | oxazole-CH$_2$-CO-O-COCl |
| 18 | H | $C_6H_5-$ | 1 | COOH | φ-CH(CO$_2$H)-COCl |
| 19 | H | $C_6H_5-$ | 1 | NH$_2$ | φ-CH(NH$_3^+$Cl$^-$)-COCl |
| 20 | H | C$_6$H$_5$ | 1 | H | C$_6$H$_5$-CH$_2$-COCl |
| 21 | H | thiophene | 1 | H | thiophene-CH$_2$-COCl |
| 22 | Na | thiane | 1 | H | thiane-CH$_2$-COCl |
| 23 | H | $C_6H_4-CH_2-$ | 1 | NH$_2$ | φ-CH$_2$-CH(NH$_3^+$Cl$^-$)-COCl |
| 24 | H | $C_6H_5-$ | 1 | $-$NHCONH$_2$ | φ-CH(OH)-COOH |
| 25 | H | 2,6-dimethoxyphenyl | 0 | — | 2,6-dimethoxybenzoyl chloride |

-continued

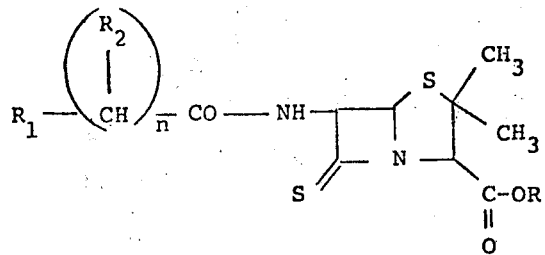

| Example | R | R₁ | n | R₂ | Acylating Agent |
|---|---|---|---|---|---|
| 26 | H | [2,6-dichlorophenyl-5-methylisoxazol-3-yl] | 0 | — | [2,6-dichlorophenyl-5-methylisoxazol-4-yl carbonyl chloride] |

What is claimed is:

1. A compound of the formula $$R_1-(CH)_n^{R_2}-CO-NH-\text{[bicyclic core]}-C-OR$$

wherein R is hydrogen, lower alkyl, phenyl-lower alkyl, trihaloethyl, alkali metal or alkaline earth metal; R₁ is hydrogen, lower alkyl, saturated or unsaturated cycloalkyl of 3 to 7 carbons, phenyl, lower alkoxyphenyl, phenoxy, phenyl-lower alkyl, thienyl, furyl, oxazolyl, isoxazolyl, or thiazolyl and said heterocyclics bearing phenyl, halophenyl, halo or lower alkyl substituents; R₂ is hydrogen, amino, carboxy or ureido; and $n$ is 0 or 1.

2. A compound as in claim 1 wherein R is hydrogen, alkali metal, trichloroethyl or —CH₂OCOR₃; R₁ is hydrogen, phenyl, thienyl or furyl; R₂ is hydrogen, amino or carboxy; and R₃ is lower alkyl.

3. A compound as in claim 1 wherein R₁ is phenyl.

4. A compound as in claim 1 wherein R₁ is thienyl.

5. A compound as in claim 2 wherein R and R₂ each is hydrogen and $n$ is 1.

6. A compound as in claim 1 wherein R and R₂ each is hydrogen and R₁ is phenoxy and $n$ is 1.

7. Alkali metal salt of the compound of claim 5.

8. Alkali metal salt of the compound of claim 6.

* * * * *